United States Patent [19]

Pradelli

[11] Patent Number: 4,781,068
[45] Date of Patent: Nov. 1, 1988

[54] DIFFERENTIAL MASS FLOWMETER

[75] Inventor: Alessandro Pradelli, Finale Emilia, Italy

[73] Assignee: Bellco SpA, Mirandola, Italy

[21] Appl. No.: 39,397

[22] Filed: Apr. 17, 1987

[30] Foreign Application Priority Data

May 6, 1986 [IT] Italy ............................. 20312 A/86

[51] Int. Cl.$^4$ .............................................. G01F 1/84
[52] U.S. Cl. .................................... 73/861.38; 73/196
[58] Field of Search .............................. 73/861.38, 196

[56] References Cited

U.S. PATENT DOCUMENTS

| | | | |
|---|---|---|---|
| 2,821,084 | 1/1958 | Altfillisch | 73/861.38 |
| 4,252,028 | 2/1981 | Smith et al. | 73/861.38 |
| 4,422,338 | 12/1983 | Smith | 73/861.38 |
| 4,658,657 | 4/1987 | Kuppers | 73/861.38 |

Primary Examiner—Herbert Goldstein
Attorney, Agent, or Firm—Guido Modiano; Albert Josif

[57] ABSTRACT

The differential mass flowmeter comprises two U-shaped tubes, arranged side by side, mutually rigidly coupled, and having their ends inserted into a support. The tubes are adapted for conveying fluid in counter-current and are provided with an electromagnet adapted for producing oscillation of the tubes about an axis passing through the portions inserted into the support, and with at least two coils, each facing a permanent magnet for generating a signal proportional to the angle of inclination of the portion of the small tubes which is opposite to the support, to thus permit continuous measurement of mass flow rate differences between two sections of a tube.

5 Claims, 2 Drawing Sheets

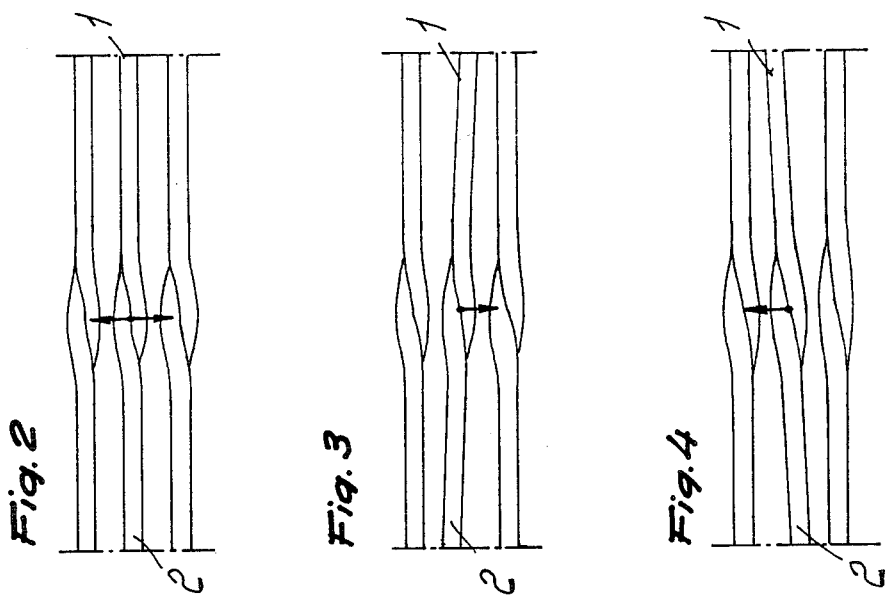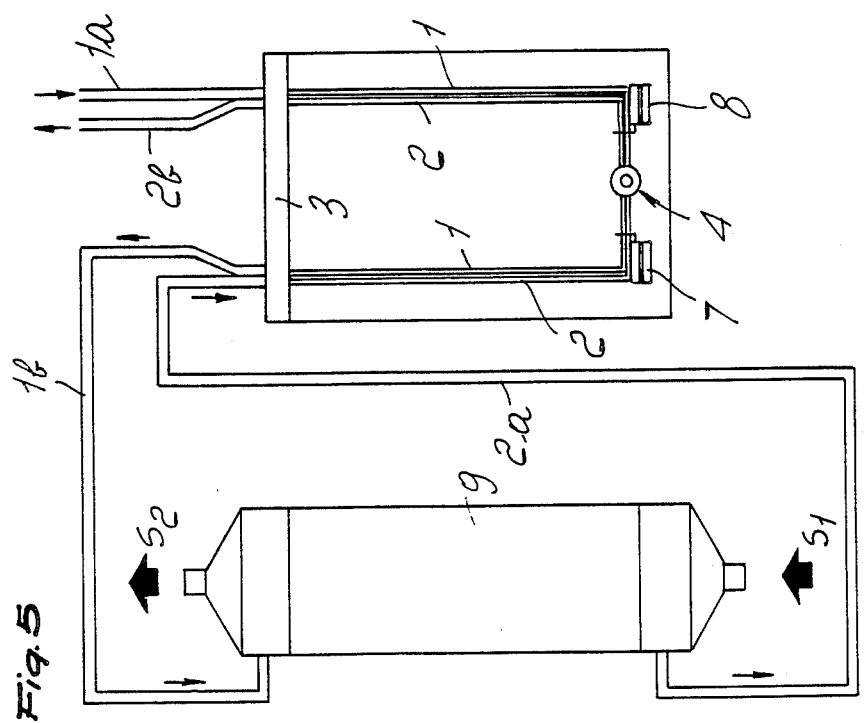

DIFFERENTIAL MASS FLOWMETER

BACKGROUND OF THE INVENTION

The present invention relates to a differential mass flowmeter.

The use is known of flowmeters comprising a substantially U-shaped tube with the ends inserted in a rigid support, which is caused to oscillate, by exploiting the elasticity of the material, about an axis passing through the portions inserted into the support.

During such oscillation, if the tube is empty, the arrangement of the portion thereof opposite the support remains unchanged, while if the tube is conveying a flow of fluid, the known Coriolis forces give rise to an inclination of said portion in one direction during the downward motion and in the opposite direction during the upward motion.

The angle of said inclination is proportional to the mass flow rate conveyed by the tube, and it is then sufficient to provide said tube with means which allow the measurement of said angle to obtain, by means of suitable signal processing, a continuous indication of said flow rate.

This kind of flowmeter is very widespread, among other applications, for the measurement of the variations which occur in the flow rate of a fluid during the passage through an apparatus; this measurement, which is performed, e.g., on the dialysis liquid entering and leaving a haemodialysis filter in order to evaluate the amount of the ultrafiltrate, i.e. the amount of water with electrolytes which passes to said liquid from the blood of a patient during its passage through the filter, is achieved by arranging one filter downstream and another one upstream of the device, but this method has many disadvantageous characteristics, such as high cost and the possibility of disturbances in the measurement.

SUMMARY OF THE INVENTION

The aim of the present invention is to provide a differential mass flowmeter which allows the continuous measurement of differences in mass flow rate between two sections of a tube, such as, e.g., the upstream section and the downstream section of an apparatus.

The aim proposed is achieved by a differential mass flowmeter, according to the invention, characterized in that it comprises at least two substantially U-shaped tubes, arranged side by side and mutually rigidly coupled, and with their ends inserted in a rigid support, which are adapted for conveying fluid in countercurrent and are provided with means adapted for producing an elastic oscillation about an axis which passes through the sections of insertion in the support, and with means adapted for generating a signal proportional to the angle of inclination assumed during oscillation of the portion of the tubes which is opposite to said support.

BRIEF DESCRIPTION OF THE DRAWINGS

Further characteristics and advantages will become apparent from the description of a preferred, but not exclusive, embodiment of the invention, illustrated only by way of non-limitative example in the accompanying drawings, wherein:

FIG. 2 is a schematic front view of the central region of the portion of the tubes which is opposite to the rigid support in three positions assumed during the oscillation in the presence of equal flow rates circulating in countercurrent in the two tubes, and precisely the upper and lower extreme positions and the middle position;

FIGS. 3 and 4 are schematic front views of the central region of the portion of the tubes which is opposite to the rigid support in three positions assumed during oscillation, respectively in the downward and upward motion, in the presence of different flow rates circulating in countercurrent in the two tubes, and precisely the upper and lower extreme positions and the middle position; and FIG. 5 diagrammatically illustrates the insertion of the invention in the circuit of the dialysis liquid of a filter for haemodialysis.

DESCRIPTION OF THE PREFERRED EMBODIMENTS

Figure 1:
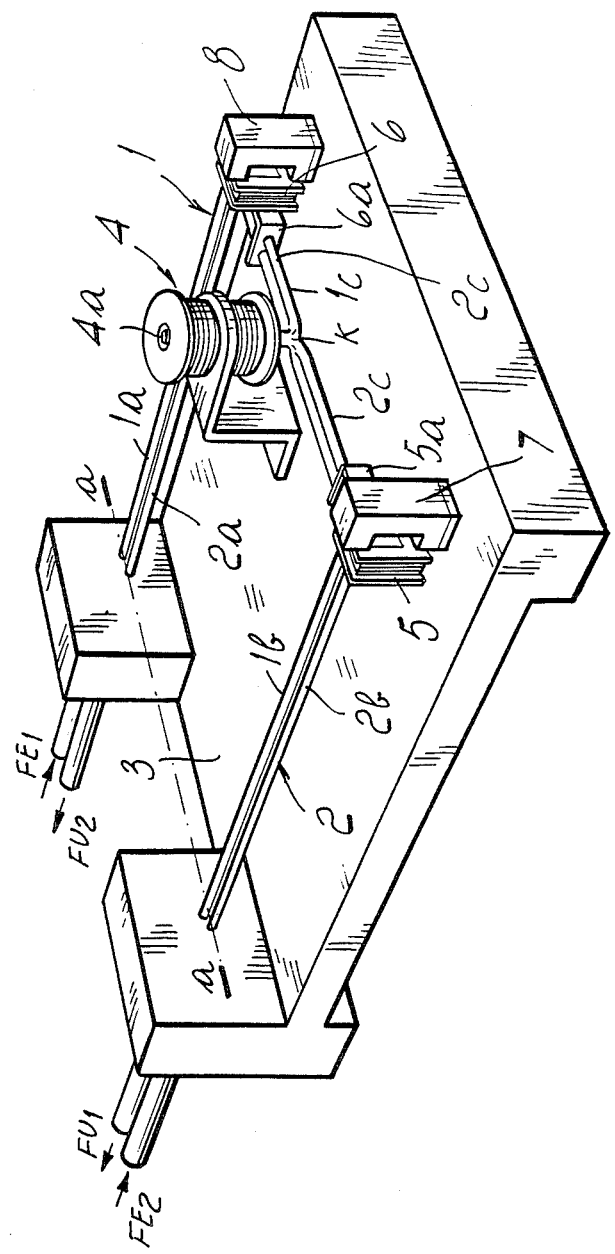
FIG. 1 is a perspective view of the invention.

With reference to the above mentioned figures, the reference numerals 1 and 2 indicate the two U-shaped tubes, arranged side by side and mutually rigidly coupled, which are provided with their ends inserted in a cantilever fashion in the rigid support 3 and are adapted for conveying fluid in countercurrent according to the arrows of FIG. 1: in the tube 1, the fluid enters along the direction of the arrow FE1 and leaves along the direction of the arrow FU1, while the fluid enters the tube 2 along the direction of the arrow FE2 and leaves along the direction of the arrow FU2.

As clearly visible from the drawing FIG. 1 the above mentioned side by side arrangement implies that the two U-shaped tubes 1 and 2 lie in a common plane. It appears further from the drawing the the U-shaped tubes have each opposite side tube portions 1a, 1b and 2a, 2b and tube portions 1c and 2c opposite to the support 3 connecting the side tube portions 1a, 1b. The above mentioned side-by-side arrangement implies further that the tube portions 1c and 2c cross each other in an intermediate point K between the side tube portions 1a, 1b and 2a, 2b, the coupling between the "U" shaped tubes 1 and 2 occuring at said cross-point K. It appears further from the drawing that the two "U" shaped tube units are coextensive with respect to each other.

The system formed by the tubes 1 and 2 is made to oscillate at its resonance frequency about the axis aa, exploiting the elasticity of the material, by means which comprise an electromagnet generally indicated with the reference numeral 4, within which the reference numeral 4a indicates the central magnet, rigidly coupled to said tubes 1 and 2.

When equal flow rates occur in the two tubes, during the oscillation the portion of the tubes which is opposite the rigid support 3 maintains a constant attitude, as illustrated in FIG. 2; instead, if the two flow rates are different, the known Coriolis forces give rise to an inclination of said portion in one direction during the downward motion and in the opposite direction during the upward motion, as illustrated in FIGS. 3 and 4, the angle of inclination thus determined being proportional to the difference of said flow rates.

The device according to the invention is then provided with means adapted for generating a signal which is proportional to said angle of inclination, comprising the coils 5 and 6 fixed by means of the brackets 5a and 6a at the ends of the portion of the tubes which is opposite to the support 3, so as to be arranged respectively facing the permanent magnets 7 and 8 rigidly coupled to the support 3; the signal departing from said coils is suitably processed by a control unit not illustrated in the figure, and since it is proportional to the angle of inclination of said tubes, on the grounds of the above it is proportional to the difference of the mass flow rates circulating in countercurrent therein.

FIG. 5 illustrates an application of the differential flowmeter to the measurement of the amount of ultrafiltration which occurs during a haemodialysis treatment, i.e. of the amount of water and electrolytes which passes into the dialysis liquid from the blood of a patient during the passage of the blood along the arrows 51 and 52 to a filter for haemodialysis 9.

The dialysis liquid originating from the conduit 1a is fed into the small tube 1 of the flow meter and emerges therefrom into the conduit 1b for conveyance to the filter 9, while the duct 2a which collects said dialysis liquid in output from the filter 9, eventually enriched with ultrafiltered water, is connected to the tube 2 of the flowmeter to emerge, when leaving the latter, into the outlet or evacuation conduit 2b; in this manner, the ultrafiltered quantity can be identified with the difference of the mass flow rate which circulates in the two small tubes, and is therefore detected continuously by means of the signal emitted by the instrument.

The insertion of the differential flowmeter to measure the amount of ultrafiltration is very advantageous with respect to the known art, which implies the insertion of two flowmeters, one at the inlet and the other at the outlet of the filter, for a number of reasons.

First of all, the number of components is greatly reduced, and only one instrument calibration is required; furthermore, there no longer exists the problem of thermal variations which may differently affect the two flowmeters, the drift caused by two electronic circuits is eliminated, and, finally, so is the beat frequency, caused by the interference present between two flowmeters which operate on the same principle and vibrate with not exactly equal frequencies.

Obviously, the application of the differential flowmeter described is not restricted to the measurement of ultrafiltrate, extending, with advantages of the kind described above, to the various fields in which it is necessary to measure differences in mass flow rates.

The invention described is susceptible to numerous modifications and variations, all of which are within the scope of the inventive concept, and in the practical embodiment of the invention all the details may be replaced with technically equivalent elements; moreover, the materials employed, as well as the dimensions and the shapes, may be any according to the requirements.

I claim:

1. A differential mass flowmeter including a pair of "U" shaped tube units mounted at the open end of the "U" to a support and extending therefrom in a cantilevered fashion and including means for oscillating the tube units relative to the support and signal generating means for generating a signal proportional to the angle of inclination assumed during oscillation by the portion of the tube units opposite to said support, wherein according to the improvement the tube units of said pair of "U" shaped tube units are arranged in a common plane and in side by side and coextensive relationship to each other and wherein the tube portions of said tube units opposite to said support comprise a cross-point in which said tube portions cross each other and in which said tube portions are coupled to each other.

2. A flowmeter according to claim 1, wherein said means for oscillating the tube units are arranged at said cross-point.

3. A flowmeter according to claim 1, wherein said means for oscillating the tube units comprise an electromagnet having a central magnet portion thereof rigidly connected to said cross point.

4. A flowmeter according to claim 1, wherein said signal generating means comprise at least two coils fixed proximate the ends of the tube portions opposite to said support of said "U" shaped units, each of said coils cooperating with a permanent magnet fixed with respect to said support and facing said coils.

5. A differential mass flowmeter including a pair of "U" shaped tube units mounted at the open end of the "U" to a support and extending therefrom in a cantilevered fashion and including means for oscillating the tube units relative to the support and signal generating means for generating a signal proportional to the angle of inclination assumed during oscillation by the portion of the tube units opposite to said support, wherein according to the improvement the tube units of said pair of "U" shaped tube units are arranged in a common plane and in side by side and coextensive relationship to each other and wherein the tube portions of said tube units opposite to said support comprise a cross-point in which said tube portions cross each other and in which said tube portions are coupled to each other and wherein said means for oscillating the tube units are arranged at said cross-point and comprise an electromagnet having a central magnet portion thereof rigidly connected to said cross point and wherein said signal generating means comprise at least two coils fixed proximate the ends of the tube portions opposite to said support of said "U" shaped units, each of said coils cooperating with a permanent magnet fixed with respect to said support and facing said coils.

* * * * *